United States Patent [19]
Gold

[11] 4,088,644
[45] May 9, 1978

[54] N-ACYL-3-AZETIDINONE

[75] Inventor: Elijah H. Gold, West Orange, N.J.

[73] Assignee: Schering-Corporation, Kenilworth, N.J.

[21] Appl. No.: 452,871

[22] Filed: Mar. 20, 1974

Related U.S. Application Data

[60] Division of Ser. No. 237,931, Mar. 24, 1972, abandoned, which is a continuation-in-part of Ser. No. 741,205, Jun. 28, 1968, abandoned.

[51] Int. Cl.$^2$ .................. C07D 205/06; C07D 205/04
[52] U.S. Cl. .............................. 260/239 A; 260/558 P
[58] Field of Search ..................................... 260/239 A

[56] References Cited

U.S. PATENT DOCUMENTS

| | | | |
|---|---|---|---|
| 3,083,208 | 3/1963 | Wu | 260/239 |
| 3,481,920 | 12/1969 | Hargrove | 260/239 A |

*Primary Examiner*—Donald G. Daus
*Assistant Examiner*—Mark L. Berch
*Attorney, Agent, or Firm*—Bruce M. Eisen; Stephen B. Coan; Raymond A. McDonald

[57] ABSTRACT

Disclosed herein are novel N-acyl-3-aryl-3-azetidinols useful as intermediates. A method is provided for their direct preparation from acyclic starting materials. These N-acyl-3-aryl-azetidinols provide a convenient route to the 3-acetidinol series.

2 Claims, No Drawings

N-ACYL-3-AZETIDINONE

This is a division, of application Serial No. 237,931, filed Mar. 24, 1972, now abandoned, which in turn is a continuation-in-part of my copending application Ser. No. 741,205, filed June 28, 1968, now abandoned.

In recent years there has been much interest in the 3-azetidinol series of compounds. Heretofore the preparation of intermediates for these compounds has been a time-consuming and tedious chore and has usually involved chemical transformations of preformed azetidinols.

It has now been found that N-acyl-3-phenyl-3-azetidinols can be easily and rapidly synthesized from acyclic starting materials.

The invention sought to be patented in its process aspect comprises the photolysis of an amino-keto acylate to yield the corresponding N-acyl-3-aryl-3-acetidinol.

This invention relates to compositions of matter having the molecular structure of azetidine in which the ring nitrogen atom is acylated and in which the 3-carbon atom in the ring is substituted by both a phenyl group and a $-OR_3$ group. These chemical compounds may optionally have a lower alkyl radical substituted in each of the 2 and 4 carbon atom positions in the azetidine ring and may also optionally have substituents on the phenyl nucleus. These compounds may be used as intermediates for preparing such compounds as N-alkyl-3-aryl-3-azetidinols which have utility per se as analgesics.

More specifically, the compounds of this invention may be represented by the structural formula:

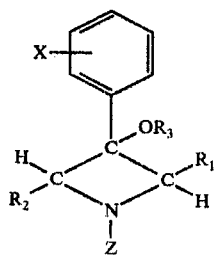

(I)

wherein $R_1$ and $R_2$ are each hydrogen or lower alkyl; $R_3$ is hydrogen, lower alkyl or a lower alkanoyl radical; X is hydrogen, fluorine, chlorine, bromine, lower alkyl, hydroxy, lower alkoxy or trifluoromethyl; and Z is acyl.

The lower alkyl radicals referred to above (including the alkyl portion of the lower alkoxy and lower alkanoyl radicals) may be straight or branched-chain cyclic and may include, for example, methyl, ethyl, n-propyl, iso-propyl, n-butyl, sec-butyl, iso-amyl, n-hexyl, cyclopropyl, cyclopentyl, cyclohexyl and the like. Exemplifying lower alkanoyl groups are isobutyryl, valeryl and caproyl.

The term acyl as used herein is used as defined in standard chemical reference sources, e.g. Hackh's Chemical Dictionary, 4th Edition (1969); The International Encyclopedia of Chemical Science (1964), and Van Nostrand's Chemist's Dictionary (1953). It may be defined as an organic radical derived from an organic acid by the removal of the hydroxyl group.

Exemplifying acyl groups are acetyl, propionyl, perfluoroethylcarbonyl, carbobenzyloxy, benzoyl, toluenesulfonyl, methanesulfonyl, and the like. Preferred acyl radicals include p-toluenesulfonyl, methylsulfonyl, benzoyl and perfluoroloweralkanoyl.

In those instances wherein the organic radical contains a phenyl moiety, said moiety may be substituted with such substituents as lower alkyl, trifluoromethyl, fluoro, chloro, bromo, hydroxy or lower alkoxy.

The compounds of formula I wherein $R_3$ is hydrogen can be prepared by the photolytic cyclization of an amino-keto acylate of formula (II) by irradiation with light having a wavelength greater than 280 μ.

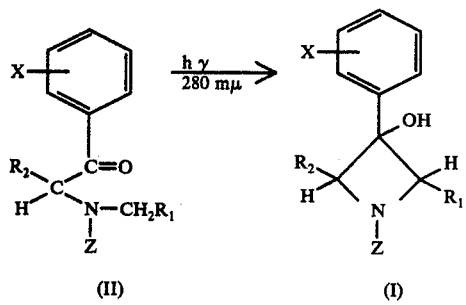

wherein
$R_1$, $R_2$, X and Z are as above defined.

The cyclization is carried out under a nitrogen atmosphere in a suitable solvent such as ether, or an alcohol, e.g. butanol and ethanol.

The reaction mixture is photolyzed until the aminoketo acylate is consumed. The resulting mixture is filtered and the crude product is generally isolated from the filtrate by such standard techniques as chromatography or crystallization. The crude product may then be purified according to standard techniques, e.g. fractional crystallization.

In an alternate manner, the compounds of formula I may also be prepared by condensing an N-acyl-3-azetidinone (III) with a phenyl-metal compound (IV) such as phenylmagnesium bromide. Compounds of formula III may be prepared by the oxidation of a corresponding 3-azetidinol.

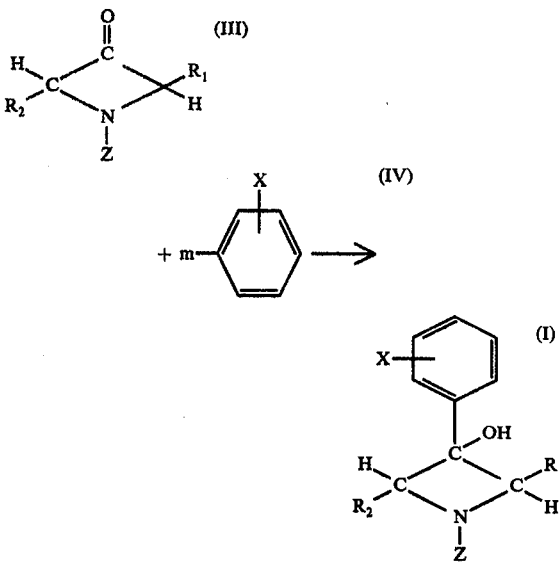

wherein $R_1$, $R_2$, X and Z are as previously defined and m is a reactive metal halide such as lithium or magnesium bromide.

The reaction is usually carried out at low temperatures (e.g. 10° to −50° C) in a suitable organic solvent such as ether. The phenyl-metal halide is usually added to the ketone in solution in a dropwise manner. The reaction is allowed to go to completion, a process usually requiring less than one hour and the reaction mixture is decomposed with a basic reagent such as 10% aqueous ammonium chloride. The resulting 3-acyl-3-aryl-3-azetidinol is then isolated and purified according to standard techniques.

In those instances wherein it is desired to have an $R_3$-substituent other than hydrogen, it may be introduced into the N-acyl-3-phenyl-3-azetidinol molecule according to standard techniques known to the art for esterifying or etherifying a hydroxyl group.

The following examples are illustrative of the preparation of representative compounds of this invention.

EXAMPLE 1

Preparation of N-benzoyl-3-phenyl-3-azetidinol

A. Preparation of N-benzoyl-3-azetidinone

To a stirred mixture of 2.5 g. of N-benzoyl-3-azetidinol, 21 g. of triethylamine in 35 ml. of DMSO, add rapidly, in a dropwise manner, a suspension of 7.0 g. of pyridine sulfur trioxide in 35 ml. of DMSO and stir for 15 minutes. Remove most of the DMSO in vacuo at 60° C and chromatograph the residue on 100 g. of silica gel. Elute with chlorform and collect 2.4 g. of the crude compound of this example from the front running yellow band. Recrystallize from isopropyl ether.

B. Preparation of N-benzoyl-3-phenyl-3-azetidinol

To a stirred solution of 1.8 gm of N-benzoyl-3-azetidinone dissolved in 20 ml. of ether at −30° C, slowly add, in a dropwise manner, 11 ml. of 0.1 N-phenylmagnesium bromide in ether. Stir for ten minutes and then decompose with 15 ml. of 10% aqueous ammonium chloride. Remove the ether phase and extract the aqueous phase twice with 40 ml. portions of ether. Dry the combined ether extracts over sodium sulfate. Filter and remove the ether in vacuo to obtain 2.0 g. of N-benzoyl-3-phenyl-3-azetidinol.

By substituting equivalent quantities of:
N-benzoyl-2-methyl-3-azetidinone,
N-mesyl-2,4-dimethyl-3-azetidinone,
N-tosyl-3-azetidinone,
N-carbobenzyloxy-3-azetidinone,
N-[γ,γ,γ-trifluoropropionyl]-2,4-diisopropyl-3-azetidinone, or N-benzoyl-2-ethyl-3-azetidinone
in place of the N-benzoyl-3-azetidinone, and by following substantially the same reaction procedure of this example, there is produced N-benzoyl-2-methyl-3-phenyl-3-azetidinol,
N-mesyl-2,4-dimethyl-3-phenyl-3-azetidinol,
N-tosyl-3-phenyl-3-azetidinol,
N-carbobenzyloxy-3-phenyl-3-azetidinol,
N-[γ,γ,γ-trifluoropropionyl]-2,4-diisopropyl-3-phenyl-3-azetidinol, and
N-benzoyl-2-ethyl-3-phenyl-3-azetidinol, respectively.

Similarly by substituting equivalent quantities of:
p-chlorophenylmagnesium bromide,
p-trifluoromethylmagnesium bromide,
o-fluorophenylmagnesium bromide,
p-methoxyphenylmagnesium bromide, or
m-ethylphenylmagnesium bromide
in place of the phenylmagnesium bromide, and by following substantially the same procedure of this example, there is produced:
N-benzoyl-3-(p-chlorophenyl)-3-azetidinol,
N-benzoyl-3-(p-trifluoromethylphenyl)-3-azetidinol,
N-benzoyl-3-(o-fluorophenyl)-3-azetidinol,
N-benzoyl-3-(p-methoxyphenyl)-3-azetidinol, and
N-benzoyl-3-(m-ethylphenyl)-3-azetidinol.

EXAMPLE 2

Preparation of N-(p-toluenesulphonyl-2-methyl-3-phenyl-3-azetidinol

In a nitrogen atmosphere, using a Hanovia 450 watt medium pressure ultraviolet lamp in a water cooled pyrex immersion well, internally irradiate 23.3 g. of N-ethyl-N-α-p-toluenesulphonamidoacetophenone dissolved in 4 liters of ether, with stirring for six hours. Filter, remove the ether in vacuo, crystallize the residue from 100 ml. of carbon tetrachloride and obtain 15.0 g. of the product of this example.

EXAMPLE 3

Preparation of N-benzoyl-3-phenyl-3-azetidinol

In a nitrogen atmosphere, using a Hanovia 450 watt medium pressure ultraviolet lamp in a water cooled pyrex immersion well, internally irradiate 16 g. of N-methyl-α-benzamidoacetophenone [J. Am. Chem. Soc., 78, 1941 (1956)] dissolved in 2.3 liters of ether, with stirring for 15 hours. Filter the solution and chromatograph the crude product, after removing most of the solvent on 900 g. of silica gel. Wash the column with about 6 liters of chloroform and then elute the desired product with 3% methanol in chloroform (containing 0.75% ethanol) and obtain 9.4 g. of solid 1-benzoyl-3-phenyl-3-azetidinol.

Using the above-described methods and employing analogous reagents, one can similarly prepare the other compounds of this invention. For example, using an $R_1$, $R_2$ mono or dialkyl-substituted amino-ketoacylate, one can prepare the corresponding 1-acyl-2-alkyl or 2,4-dialkyl-3-phenyl-3-azetidinols. For example, by substituting for the N-methyl-α-benzamidoacetophenone reactant of the above example:
N-(1-isobutyl)-N-α-p-toluenesulfonamidoacetophenone,
α-[N-ethyl-N-p-toluenesulfonamido]-propiophenone, or
N-propyl-N-α-toluenesulfonamidoacetophenone, one may obtain:
N-tosyl-2-isopropyl-3-phenyl-3-azetidinol,
N-tosyl-2,4-dimethyl-3-phenyl-3-azetidinol, and
N-tosyl-3-ethyl-3-phenyl-3-azetidinol, respectively.

EXAMPLE 4

Preparation of N-trifluoromethylacetyl-3-phenyl-3-azetidinol

A. Preparation of N-methyl-N-trifluoroacetyl-α-aminoacetophenone

Add 23.1 g. of trifluoroaceticanhydride to 14.9 g. of N-methyl-α-acetaminoacetophenone in 65 ml. of dichloromethane. Reflux the mixture for one hour. Wash the solution with saturated sodium bicarbonate and then with water. Dry over magnesium sulfate, filter and remove the solvent in vacuo and obtain the product of this step.

B. Preparation of N-trifluoromethylacetyl-3-phenyl-3azetidinol

In a nitrogen atmosphere using a Hanovia 450 watt medium pressure ultraviolet lamp in a water cooled pyrex immersion well, internally irradiate 1.0 g. of N-methyl-N-trifluoroacetyl-α-aminoacetophenone dissolved in 250 ml. of ether, with stirring for 1 hour. Filter and isolate the product of this example.

Similarly by replacing the N-methyl-N-trifluoroacetyl-α-aminoacetophenone reactant with equivalent quantities of N-methyl-N-pentafluoroethylacetyl-α-aminoacetophenone; N-methyl-N-difluoromethylacetyl-α-aminoacetophenone; and N-methyl-N-propionyl-α-aminoacetophenone, and following substantially the same procedure of this example there is produced the corresponding 1-acylated-3-phenyl-3-azetidinol.

EXAMPLE 5

Preparation of N-carbobenzyloxy-2-methyl-3-phenyl-3-azetidinol

A. Preparation of N-carbobenzyloxy-N-ethyl-α-amino-acetophenone

Add, in a dropwise manner, 20.4 g. of carbobenzyloxy chloride to a stirred ice-cooled mixture of 16.3 g. of N-ethyl-α-aminoacetophenone hydrochloride and 12.7 g. of sodium carbonate in 125 ml. of water and maintain the reaction temperature at about 20°-25° C. When the addition is complete, stir for one hour at room temperature and extract the product with ether. Wash the ether extract successively with 5% hydrochloric acid, water saturated aqueous sodium bicarbonate and finally with water. Dry over magnesium sulfate and filter. Remove the ether in vacuo and obtain the product of this step.

B. Preparation of N-carbobenzyloxy-2-methyl-3-phenyl-3-azetidinol

In a nitrogen atmosphere using a 450 watt Hanovia medium pressure ultraviolet lamp in a water-cooled pyrex immersion well, internally irradiate 1.5 g. of N-carbobenzyloxy-N-ethyl-α-aminacetophenone dissolved in 250 ml of ether. Stir for 1 hour. Filter, and isolate the product of this example.

EXAMPLE 6

Preparation of N-methanesulfonyl-3-phenyl-3-azetidinol

A. Preparation of N-methanesulfonyl-N-methyl-α-aminoacetophenone

To a stirred, ice-cooled, mixture of 13.1 g. of 2-(N-methylaminomethyl)-2-phenyl-1,3-dioxolane and 14.8 g. of sodium carbonate in 100 ml. of dry acetonitrile, add 12.1 g. of methanesulfonyl chloride in 25 ml. of dry acetonitrile over a 10 minute period. Remove the cooling bath and stir for two hours. Cool in an ice bath and add 140 ml. of 5% aqueous sodium hydroxide. Separate the layers, wash the aqueous layer once with dichloromethane, combine the organic extracts and remove the solvent in vacuo to give the compound of this step.

To this stirred residue, add 50 ml. of methanol and 10 ml. of 6N-hydrochloric acid and reflux for two hours. Cool and filter off the product of this reaction.

B. Preparation of N-methanesulfonyl-3-phenyl-3-azetidinol

Using a Hanovia 450 watt medium pressure ultraviolet lamp, and under a nitrogen atmosphere, in a water cooled pyrex immersion well internally irradiate 1.5 g. of N-methanesulfonyl-N-methyl-α-aminoacetophenone dissolved in 250 ml. of ether. Irradiate the mixture for 50 minutes. Filter and reduce the volume to about 10 ml. whereupon the desired compound crystallizes out. Recrystallize from a chloroform-hexane mixture obtaining the compound of this example.

By substituting equivalent quantities of:
N-cyclopropylcarbonyl-N-methyl-α-aminoacetophenone,
N-trifluoromethylsulfonyl-N-methyl-α-aminoacetophenone,
N-methoxycarbonyl-N-methyl-α-aminoacetophenone,
N-tosyl-N-methyl-α-aminoacetophenone,
N-phenethylcarbonyl-N-methyl-α-aminoacetophenone, and
N-benzylsulfonyl-N-methyl-α-aminoacetophenone, for the N-methylanesulfonyl-N-methyl-α-aminoacetophenone of the above example, and by the following substantially the same procedure there is produced:
N-cyclopropylcarbonyl-3-phenyl-3-azetidinol,
N-trifluoromethylsulfonyl-3-phenyl-3-azetidinol,
N-methoxycarbonyl-3-phenyl-3-azetidinol,
N-tosyl-3-phenyl-3-azetidinol,
N-phenethylcarbonyl-3-phenyl-3-azetidinol, and
N-benzosulfonyl-3-phenyl-3-azetidinol, respectively.

Numerous variations of the above examples will be apparent to one skilled in the art of chemistry, and as such are contemplated as being within the scope of this invention.

The N-acyl-3-phenyl-3-azetidinols of this invention may be deacylated according to standard techniques such as hydrolysis, electrolysis, or reductive cleavage. In those instances wherein the acyl moiety is an aryl sulfonyl group electrolysis is the preferred deacylation technique. When the acyl moiety is a sulfonyl group, metal hydride reductive cleavage is preferred, after suitably protecting the alcohol moiety.

The free 3-aryl-3-azetidinols may be N-alkylated in a variety of manners. For example, it can be condensed at ambient temperatures with an appropriate oxo-derivative of the desired N-alkyl moiety in an inert organic solvent, such as ethanol, to yield the corresponding imine condensate. THe latter can be reduced in situ, and may, for example, be conducted catalytically by hydrogenation over a palladium catalyst in a suitable solvent. Exemplifying the oxo-compound are formaldehye, acetaldehyde, acetcyclohexylacetaldehyde, 4-methylcyclohexanone and the like.

Other N-alkyl, or aralkyl derivatives may be produced directly by reduction of the suitable Z radicals. For example, to directly produce a N-benzyl-3-phenyl-azetidinol, the acyl group Z can be benzoyl and the desired compound can be produced directly by standard reduction methods. e.g., lithiumaluminum hydride in tetrahydrofuran.

It is, of course, recognized that the compounds of this invention embrace geometric isomers when either or both $R_1$ and $R_2$ are alkyl. The compounds of this invention also exhibit steroisomerism.

I claim:

1. A compound having the structural formula:
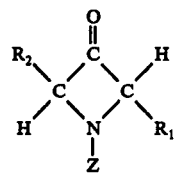
wherein $R_1$ and $R_2$ are each hydrogen or lower alkyl; and Z is an acyl moiety derived from a carboxylic acid or sulfonic acid by removal of the hydroxyl group.
2. A compound of claim 1, which is N-benzoyl-3-azetidinone.
* * * * *